United States Patent [19]

Daugherty

[11] Patent Number: 4,661,300
[45] Date of Patent: Apr. 28, 1987

[54] METHOD AND APPARATUS FOR FLASHLESS TIPPING OF AN I.V. CATHETER

[75] Inventor: Charles W. Daugherty, Xenia, Ohio

[73] Assignee: Becton, Dickinson and Company, Franklin Lakes, N.J.

[21] Appl. No.: 838,739

[22] Filed: Mar. 11, 1986

Related U.S. Application Data

[63] Continuation of Ser. No. 649,567, Sep. 12, 1984, abandoned.

[51] Int. Cl.$^4$ ............................................. B29C 31/08
[52] U.S. Cl. .................................. 264/40.6; 264/163; 264/320; 425/144; 425/145; 425/298; 425/384; 425/393
[58] Field of Search ...................... 264/320, 322, 40.1, 264/40.6, 40.7, 163; 425/393, 383, 384, 392, 397, 398, 406, 145, 144, 298; 308/30 A, 5 R

[56] References Cited

U.S. PATENT DOCUMENTS

| | | | |
|---|---|---|---|
| 3,475,786 | 11/1969 | Pearson | 425/143 |
| 4,114,959 | 9/1978 | Christ | 308/3.5 |
| 4,292,270 | 9/1981 | Hannah et al. | 264/320 |
| 4,373,894 | 2/1983 | Peppel | 425/393 |
| 4,404,159 | 9/1983 | McFarlane | 264/296 |

Primary Examiner—Jan Silbaugh
Assistant Examiner—Mary Lynn Fertig
Attorney, Agent, or Firm—A. Passman

[57] ABSTRACT

A method and apparatus for tipping one end of an I.V. catheter includes the method steps for use of the apparatus including mounting a catheter to be tipped onto a mandrel supported on a carriage; a die having an interior molding surface, at least one portion of which is tapered according to the tip desired on the catheter, is heated; the carriage is moved along guide bars to the die such that the catheter carrying mandrel moves toward the interior molding surface to define a space, when the carriage is halted the catheter carrying mandrel is biased toward the die space with only sufficient force to cause the heated catheter to flow into the die space and as the catheter melts and flows, the mandrel engages the die thereby defining the edge of the catheter, after which the die and catheter therein are cooled; the carriage is then reversed along the guide bars such that the catheter and mandrel are withdrawn from the die, and the catheter is removed from the mandrel. An apparatus for performing the above described method is also disclosed.

7 Claims, 5 Drawing Figures

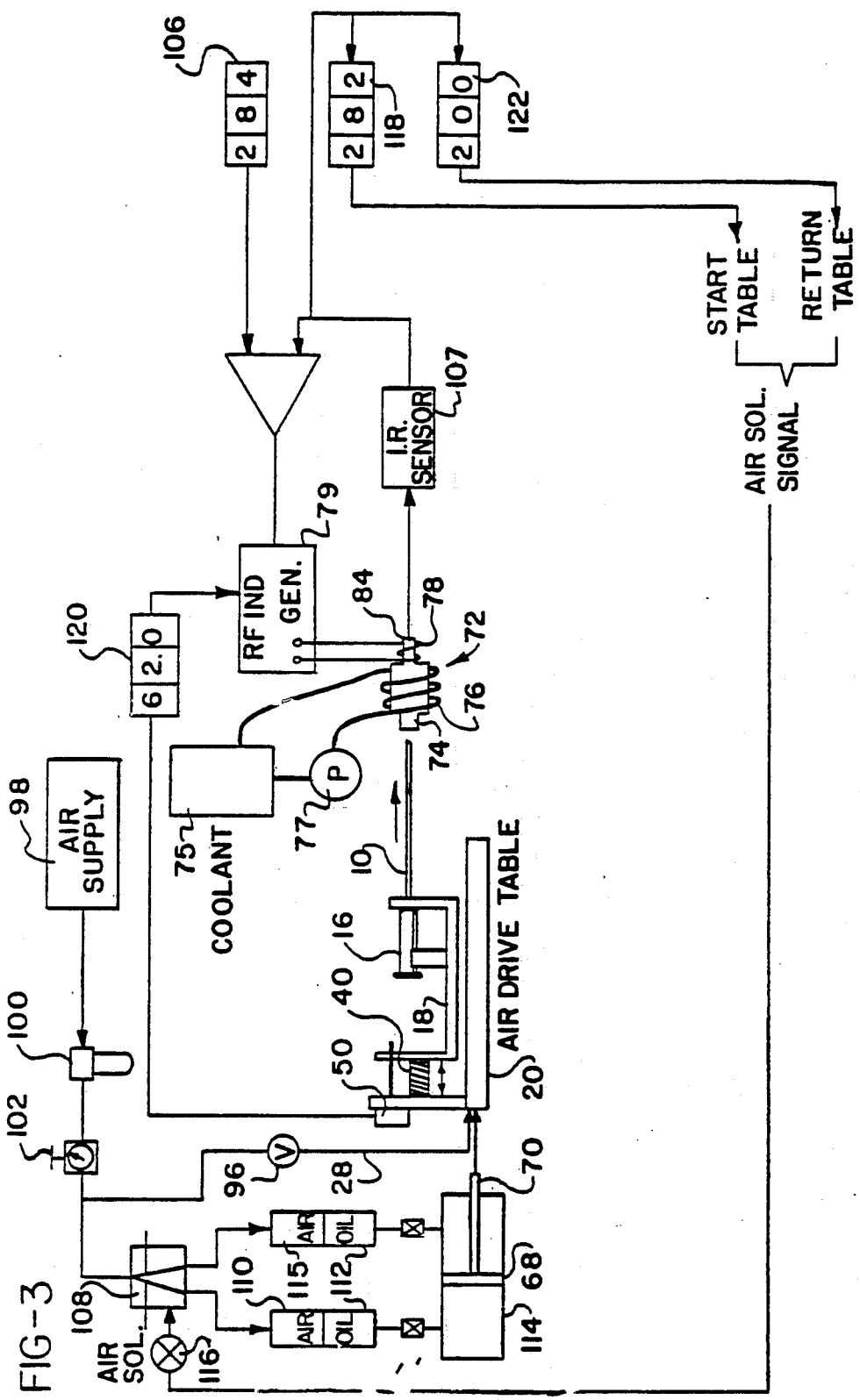

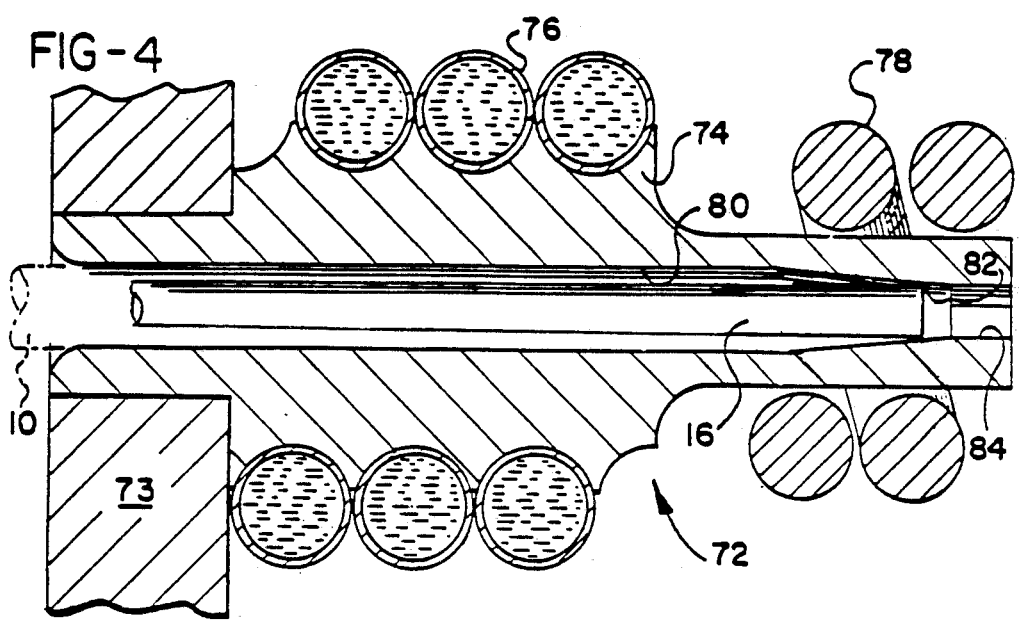
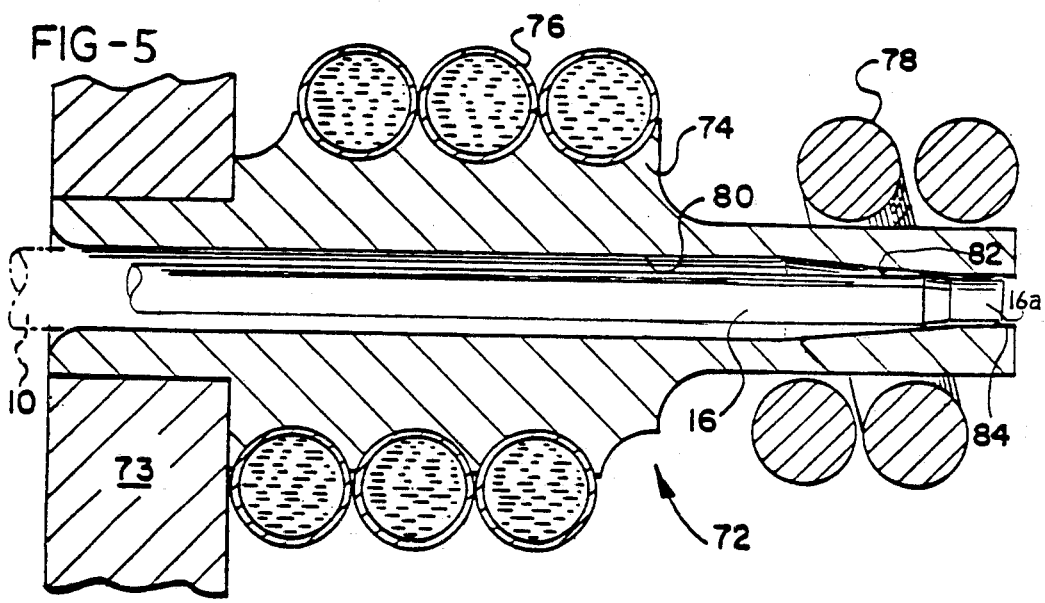

METHOD AND APPARATUS FOR FLASHLESS TIPPING OF AN I.V. CATHETER

This is a continuation of co-pending application Ser. No. 649,567 filed on Sept. 12, 1984 now abandoned.

BACKGROUND OF THE INVENTION

The present invention relates to a method and apparatus for flashless tipping of an I.V. catheter and, more particularly, to a method and apparatus for forming a tapered tip on a thin wall catheter constructed of a polyurethane plastic material.

Intravenous (I.V.) catheters are particularly used in medical applications for directing blood, plasma, or other fluids into the circulatory system of a patient. While I.V. catheters are available in several different types, one common type of catheter is constructed so as to be mounted upon a relatively long, hollow cannula with a slight friction fit. A hub is attached at one end of the catheter and is designed so as to be connectable with and detachable from an I.V. fluid supply line. To insert the catheter into the patient, the cannula and catheter together are inserted through the patient's skin, whereupon the cannula may be withdrawn, leaving the catheter in place.

As manufactured, catheters have distal ends, being those ends to be inserted through the skin, those are generally blunt. The use of a catheter with such a distal or leading end is not desirable since the blunt tip tends to resist insertion into the skin, thereby increasing the difficulty and trauma of insertion. Moreover, insertion of a catheter with a blunt tip increases the irritation to the surrounding tissue, and perhaps most importantly, adds significantly to the pain and discomfort of the patient during use.

Consequently, others in the past formed tapered tips on an I.V. catheter to eliminate the aforementioned problems. The methods for providing such a tip, however, are relatively few and not publicly known. Moreover, polyurethane catheters are particularly difficult to form, and thus there is no presently known method whereby a tapered tip may be formed on a polyurethane catheter.

Accordingly, it is seen that a method for tipping an I.V. catheter, and in particular a polyurethane catheter, is needed. Such a method would provide a uniform tapered tip and would be sufficiently quick and simple as to permit tipping of catheters in large quantities without any flash to remove.

SUMMARY OF THE INVENTION

A method of tipping one end of an I.V. catheter, preferably a catheter made of a thermoplastic polyurethane, includes mounting the catheter to be tipped onto a mandrel supported on a carriage. A die having an interior molding surface, with at least one portion of which is tapered according to the tip desired on the catheter, is aligned axially with the mandrel. The carriage is moved along a guide means toward the die such that the end of the catheter to be tipped engages the interior molding surface. The carriage is halted at a point after the catheter has engaged the tapered portions of the interior molding surface of the die, and is biased toward the die with only sufficient force to cause the catheter to move further into the die as the catheter is heated by RF energy to its melting point and begins to flow. The catheter is then allowed to heat in the die and is moved into the die as it begins to melt and flow under the biasing force. The mandrel is positioned so that its distal corner is against the tapered portion of the die, thus cleanly forming the leading edge of the catheter. The die and catheter therein are then cooled, and the carriage is reversed along the guide means such that the catheter is withdrawn from the die. Finally, the catheter is removed from the mandrel. There is no flash left on the leading edge because of the contact between mandrel and die. The foregoing method is conducted such that the catheter is isolated from forces extraneous to those required to mold the catheter tip.

The heating of the die is preferably performed by radio-frequency heating, but other means can be used. Additionally, the die may be cooled by passing water through a length of tubing, a portion of which is coiled about the outer periphery of the die. The water passing through the tubing contains a coolant added thereto and may be continuously recycled through the length of tubing by a water pump means.

The method may further include passing the water and coolant through the length of tubing throughout the entire tipping operation. Following removal of the catheter from the mandrel, no portion need be cut from the tipped end of the catheter to produce a uniform leading edge at the tip.

The carriage may be supported by and movable on an air table having a plurality of orifices along a top surface and inner sides thereof for applying streams of compressed air to a bottom surface and sides of the carriage. The carriage is carried by the air table such that the carriage is moved toward and away from the die by movement of the air table along a predetermined path so long as axial alignment is maintained between the mandrel and the die. The carriage is biased into the die by a spring connected between the carriage and the air table. Further, the catheter is coated with a lubricating agent prior to the engagement thereof with the die, so as to facilitate insertion into and removal from the die. While a specific mechanism for movement of the catheter and mandrel into the die is shown, skilled artisans recognize that the die could be moved toward the mandrel and catheter. Likewise, the mandrel can have a specific end shape for facilitating the flashless forming of a catheter tip.

The method may include receiving measurements from a measuring device during such time as the catheter is engaged with the die, so as to determine sufficient flow of the catheter to produce the desired tip. Upon receipt of a predetermined measurement, heating of the die is terminated and the die and catheter are cooled. The measuring device may be responsive to either the distance the catheter is biased into the die, or the time the catheter is engaged with the interior molding surface of the die. The measurements are received by a control means that automatically terminates heating of the die upon receipt of the predetermined measurement.

Apparatus for tipping one end of an I.V. catheter includes a die defining an interior molding surface therein having at least one portion of which is tapered according to the tip desired on the catheter. A means for controllably heating the die to a temperature sufficient to cause the catheter to melt and flow therein is provided, along with a means for cooling the die. A mandrel for supporting and carrying the catheter is itself supported and carried by a carriage movable along a predetermined path for inserting the catheter partially into the die and for removing the catheter from the die following production of the desired tip. A guide means retains the carriage within the predetermined path, and a reversible drive means controllably moves the carriage so as to insert partially into or remove the mandrel and the catheter from the die. Additionally, a means for biasing the mandrel and the catheter inwardly with respect to the die is included, biasing the catheter with only sufficient force to cause it to move inwardly with respect to the die as the catheter is heated to its melting point and begins to flow.

Accordingly, it is an object of the present invention to provide a method for tipping an I.V. catheter that includes moving a catheter mounted onto a mandrel supported by a carriage into a heated die, halting the carriage while biasing the catheter and mandrel further into the die, allowing the catheter to heat and flow in the space defined by the mandrel and die, cooling the die and the catheter, and removing the catheter from the die.

A further object of the present invention is to provide such a method that will provide a uniformly tapered tip to a catheter so as to facilitate insertion thereof and lessen pain and discomfort to the patient.

A still further object is to provide such a method that will enable catheters to be tipped in relatively large quantities.

Still further objects are to provide such a method which is suitable for use with polyurethane catheters and to provide an apparatus capable of tipping I.V. catheters by the method disclosed herein.

Other objects and advantages of the invention will be apparent from the following description, the accompanying drawings, and the appended claims.

BRIEF DESCRIPTION OF THE DRAWINGS

FIG. 3 is a schematic block diagram view of the apparatus showing its operation;

FIG. 4 is a sectional view of the die with the mandrel positioned all the way therein to define the space into which the heat catheter flows during tipping; and FIG. 5 is a sectional view of the die with an alternate mandrel positioned all the way therein, and that mandrel includes an extended pilot to center that mandrel.

DETAILED DESCRIPTION OF THE PREFERRED EMBODIMENT

Figure 1:
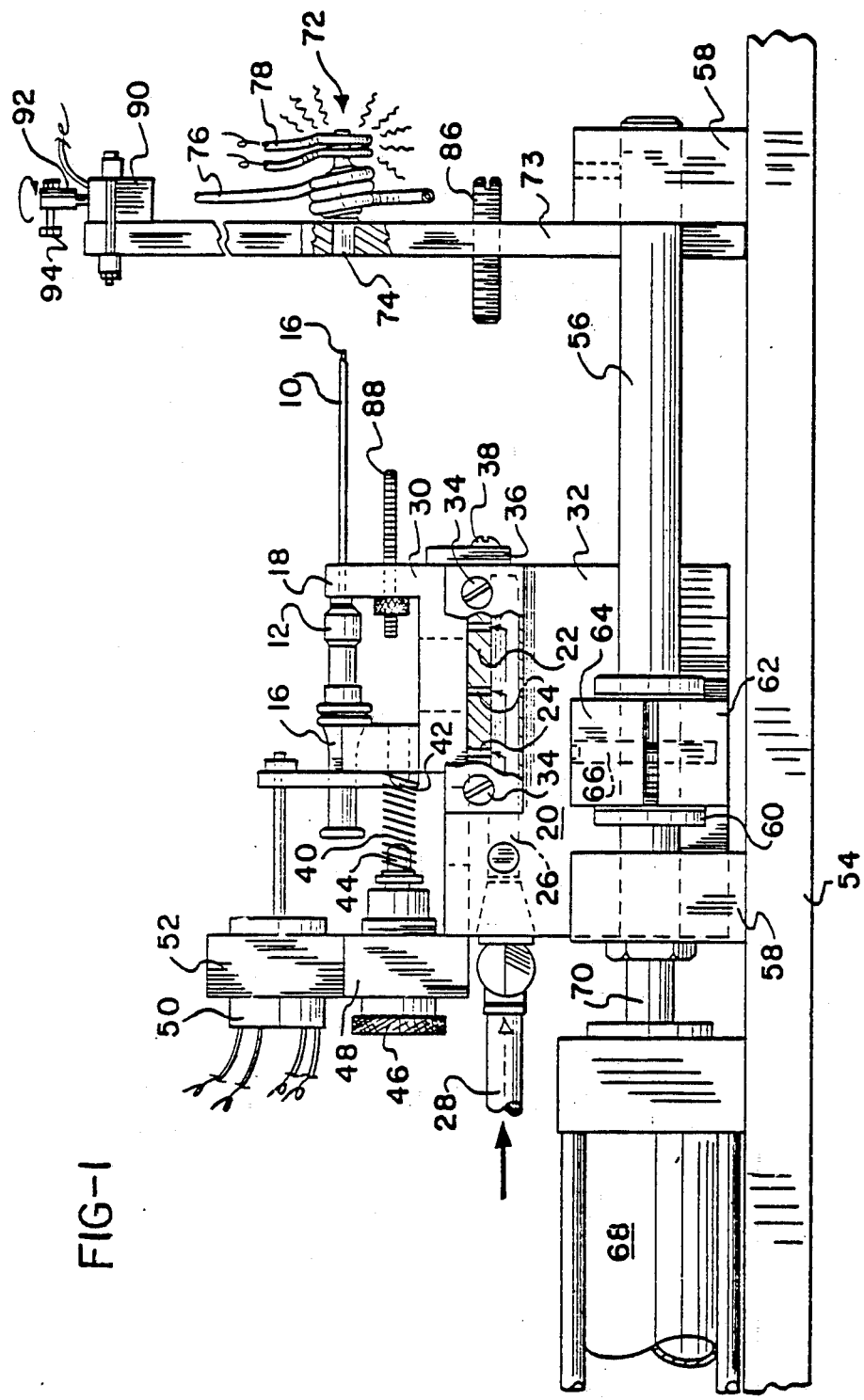
FIG. 1 is a side elevational view of a portion of the apparatus of the present invention prior to tipping of the catheter mounted thereon.

Referring to FIG. 1, a catheter 10 including a hub 12 is mounted onto a mandrel 16. As shown in FIG. 1, mandrel 16 includes a long needle-like projection extending beyond the length of the catheter 10. The outside diameter of the mandrel projection is slightly smaller than the outer diameter of the cannula (not shown) with which catheter 10 is ultimately assembled for use, thereby producing a slight friction fit when the catheter 10 is mounted to its cannula.

Mandrel 16 is mounted to and supported by a carriage 18, which is in turn supported by an air table 20. Air table 20 includes an upper surface plate 22, with a plurality of air orifices 24 defined therein. Upper surface plate 22 further defines a portion of an air passageway 26 contained within the air table 20. Air passageway 26 is connected at an outlet to an air supply line 28 for controllably admitting compressed air into the air passageway 26.

Lower surface plate 30 of carriage 18 rests atop upper surface plate 22 of air table 20. Air table 20 further includes side plates 32 attached to upper surface plate 22 by transverse screws 34. The uppermost edges of side plates 32 extend slightly above upper surface plate 22 and have additional air orifices (not shown) defined along the inner surface thereof. Such orifices communicate with air passageway 26 so as to form pressure plates for retaining and centering carriage 18 atop air table 20. Additionally, a forward retaining member 36 is attached to upper surface plate 22 by screws 38 (only one of which is shown), also for retaining carriage 18 atop air table 20.

When compressed air is supplied by an air supply line 28 to air passageway 26, it will be directed by air orifices 24 against the bottom and lower sides of lower surface plate 30 of carriage 18, thereby creating an air cushion between carriage 18 and air table 20. The space defined by side pressure plates 32 and retaining member 36 is slightly larger than lower surface plate 30. Thus, carriage 18 is supported on a frictionless surface and is freely movable thereon, to the extent permitted by side plates 32 and retaining member 36.

A means for biasing mandrel 16 in the form of spring 40 is connected between air table 20 and carriage 18. Spring 40 is fitted at one end over pin 42 on carriage 18 and at the other end over pin 44. Pin 44 is in turn mounted to a screw 46 carried by mounting block 48 attached to air table 20. Screw 46 is movable within mounting block 48, so as to impart a desired amount of tension to spring 40. Sufficient compression force will be given to spring 40 that carriage 18 will be normally biased thereby to a position against retaining member 36, as shown in FIG. 1. The relative position of carriage 18 with respect to air table 20 is determined by a measuring device comprising a linear transducer 50, mounted to a mounting member 52 attached to air table 20, and connected to carriage 18.

Air table 20 is movable with respect to a base plate 54 (see FIG. 1). A guide means for such movement, which also serves as a support means for air table 20, includes a pair of guide bars 56 mounted to base plate 54 by blocks 58; one guide bar 56 disposed on each side of air table 20. Only one of the guide bars 56 is visible in the side view of FIG. 1. Air table 20 is slidably mounted to each guide bar 56 by a sleeve member 60. Each sleeve member 60 is attached to a side plate 32 by upper and lower blocks 62 and 64. Lower block 62 is fixedly mounted to side plate 32, while upper block 64 is mounted to lower block 62 by a depending screw 66.

Figure 2:
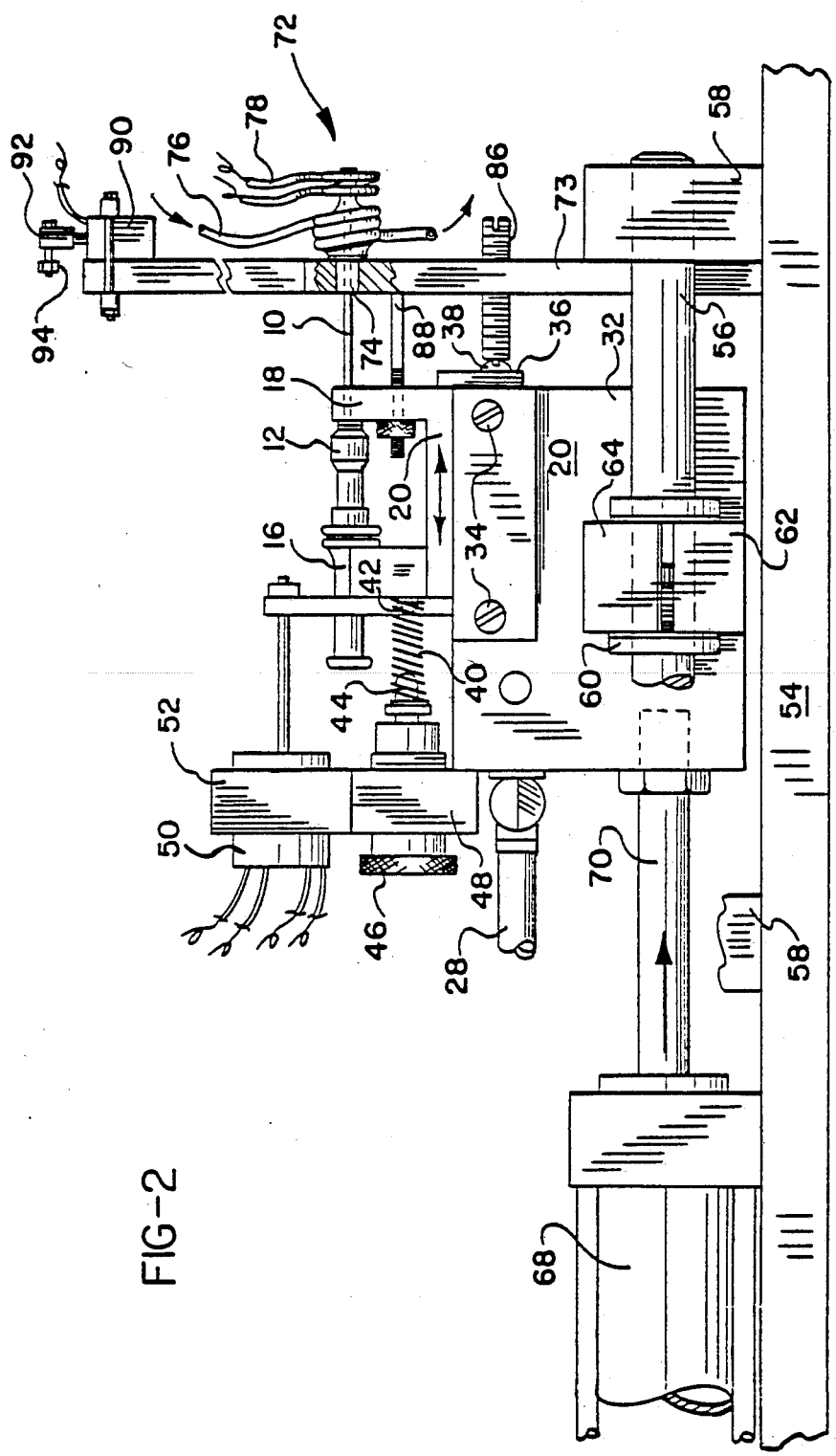
FIG. 2 is the view of FIG. 1 showing the position of the apparatus during the cooling of the die and catheter.

Air table 20 is movable along guide bars 56 by a reversible drive means including a hydraulic piston 68 which has a shaft 70 attached to air table 20. Piston 68, through shaft 70, advances air table 20 from a position as shown in FIG. 1 to a position as shown in FIG. 2 and vice versa.

Referring again to FIG. 1, the catheter 10, as carried by mandrel 16 is properly aligned axially for insertion into a die assembly 72. A mounting wall 73 supports die assembly 72, and wall 73 is in turn mounted to base plate 54. Die assembly 72 includes a die 74 and a cooling coil 76 comprising a length of tubing coiled about die 74. Cooling coil 76 is a portion of a die cooling means for circulating a cooling liquid, preferably water with a coolant added thereto, through the coil 76 for cooling the die 74. The remainder of the die cooling means, shown schematically in FIG. 3, includes a cooling liquid supply tank 75 and a recirculating pump means 77 for recirculating the cooling liquid through the cooling coil 76. Alternatively, the die cooling means may simply include a standard tap water supply source to which the cooling coil 76 is connected. Water from the supply source is passed through the coils 76 and then carried to an appropriate drain means. The die assembly 72 further includes a means for heating the die 74 having a heater coil 78. Coil 78 also surrounds die 74 and, as in the embodiment illustrated, is connected to a radio-frequency generator 79.

The die and mandrel assembly 72 is shown in greater detail in FIGS. 4 and 5. Die 74 defines an interior surface 80 therein which has a tapered molding portion 82 that is tapered according to the tip desired on the catheter 10. Additionally, interior surface 80 defines an opening 84 in die 74 near the tapered surface 82. With the exception of tapered surface 82, the interior surface 80 defines a cylindrical cavity within die 74, the diameter of which is substantially the same as the outside diameter of catheter 10. Thus, it can be appreciated that catheter 10 may be easily carried on the mandrel into die 74, but only until the tip of catheter 10 reaches the tapered surface 82. In FIG. 5 an alternate mandrel 16 configuration is shown and the difference being that the tip 16a of the mandrel 16 has a pilot extension which is of a diameter appropriate to fit freely within opening 84 thereby guiding and aligning the mandrel 16. Recognize, however, that in certain applications the tip 16a will interfere with the residual polyurethane clipped from the catheter 10 during tipping and, thus, the arrangement of FIG. 4 is preferred.

Returning to FIG. 1, an air table stop screw 86 is mounted through mounting wall 73. Stop screw 86 cooperates with one of the screws 38 on air table 20 to provide a limit to the movement of air table 20 towards die assembly 72. A carriage stop screw 88 is mounted to carriage 18. Stop screw 88 cooperates with mounting wall 73 to provide an adjustable limit to biasing of carriage 18 by spring 40. Screws 86 and 88 are adjusted to permit the mandrel 16 to seat within the tapered surface 82 whereby a space is defined in the die 74.

If necessary, a means for imparting a vibration to the die 74 can be mounted to mounting wall 73 and includes an electric motor 90. Motor 90 drives a shaft 92 to which an eccentric weight 94 is attached, thereby vibrating mounting wall 73 and die 74 attached thereto. Vibration of the die is provided so as to prevent the catheter 10 from becoming stalled within the die 74 as the catheter is inserted thereinto.

The method of tipping one end of catheter 10 may be understood by referring to FIG. 3 which illustrates the apparatus in schematic form. Initially, recirculating pump means 77 is energized, beginning circulation of the cooling liquid from supply tank 75, through coil 76, and back to supply tank 75.

Motor 90 is then energized, rotating shaft 92 and the weight 94 positioned eccentrically thereon. Rotation of shaft 92 and weight 94 imparts a vibration to die 74 to insure that a catheter 10 mounted to mandrel 16 does not become stalled upon insertion into die 74.

The catheter 10 to be tipped is mounted to be even with or to extend slightly beyond the mandrel 16, which is supported cantilever by carriage 18. Catheter 10 is first coated with a lubricating agent, preferably a silicone lubricant, to facilitate its insertion into and removal from die 74. An air table supply line valve 96 is then opened, allowing compressed air from an air supply 98 to be filtered by filter 100 and passed through regulating valve 102, to enter air table supply line 28. The compressed filtered air is directed into air passageway 26 of air table 20 and through air orifices 24, thereby creating an air cushion between air table 20 and carriage 18 (shown in FIG. 1).

The radio-frequency generator 79 is labeled in FIG. 3 RF IND GEN. and is energized to begin heating of die 74. An adjustable temperature control 106 mounted to a control panel (not shown) is provided to control generator 79 such that die 74 is heated to a temperature only sufficiently high that the catheter 10 will just begin to melt and flow within die 74. Generator 79, after heating die 74 to the proper operating temperature, is controlled to maintain die 74 at that temperature by signals provided by an infrared sensor 107. Sensor 107 is disposed so as to receive infrared radiation eminating from opening 84 of die 74 and is connected to generator 79 so as to control the same. Of course, on the alternate embodiment of FIG. 5, a direct contact temperature transducer can be used.

Once the radio-frequency generator 79 has heated die 74 to the proper temperature, the catheter 10 is moved into contact with molding surface 82 of die 74 by movement of air table 20, carriage 18 and mandrel 16 towards die 74.

Air table 20 is moved forward by hydraulic piston 68, connected to air table 20 by shaft 70. Compressed air from air supply 98, passed through filter 100 and regulating valve 102, is directed by a four-way solenoid valve 108 into the upper portion of chamber 110 that is partially filled with oil 112. The compressed air entering chamber 110 forces the oil 112 therein into the cylinder 114, thereby moving piston 68 so as to drive air table 20 towards die 74. Oil contained within cylinder 114 opposite piston 68 is forced into oil chamber 112 located beneath an air chamber 115, whereupon air contained within the upper portion of air chamber 115 is vented to an exhaust connected to air chamber 115 by valve 108.

It will be recognized that the use of both air and oil to move piston 68 is advantageous in that providing a source of compressed air is generally less expensive and complex than providing means for pumping the oil. The use of compressed air alone, however, to move piston 68 would be undesirable due to the compressibility of the air. Thus, use of both air and oil provides a smooth, uniform and controllable movement of air table 20.

Valve 108 is actuated by a solenoid 116. Signals from infrared sensor 107 are supplied to a control means (not shown) that includes adjustable temperature control 118. When the sensor 107 senses a temperature within die 74 corresponding to that indicated by temperature control 118, solenoid 116 will be energized to actuate valve 108 to direct air into chamber 110 and to exhaust chamber 115. Thus, temperature control 118 operates to cause air table 20 to be automatically moved towards die 74 upon the reaching of a proper die start-up temperature. As with temperature control 106, the numerals shown by temperature control 118 are merely approximations of actual die temperature, and the appropriate setting thereon is to be experimentally determined.

Air table 20 is moved by piston 68 until physically prevented by contact of stop screw 86 with a screw 38, as shown in FIG. 2. As air table 20 is moved towards die 74, catheter 10 and mandrel 16 move into the interior surface 80 of die 74 and are moved inwardly until the catheter tip touches the tapered surface 82. This will occur prior to halting of air table 20 by stop screw 86, however, and thus while air table 20 continues to move, carriage 18 is held stationary with respect to base plate 54 and die 74. Spring 40 is thereby compressed and consequently biases catheter 10 and mandrel 16 inwardly with respect to die 74. Thus, compression of spring 40 is determined by stop screw 86 and the resulting biasing force must be such as to move catheter 10 and mandrel 16 into die 74 only after the tip of catheter 10 begins to melt and flow. Otherwise, if the biasing force is too strong, too much catheter material will be shoved into the die and/or the tip will be crimped and misformed.

The catheter 10 is permitted to remain within molding cavity 80 of die 74 so that the tip of the catheter 10 begins to melt and flow therethrough. As the catheter tip flows, the biasing provided by spring 40 moves the catheter 10 and mandrel 16 further into the die 74 and, in particular, into the space defined between the mandrel 16 and the tapered surface 82. The linear transducer 50, mounted to air table 20, monitors this movement of catheter 10 and displays the same by a digital readout 120. While the numerals shown on temperature control 106 in FIG. 3 are intended to represent, by way of example, a temperature setting in degrees C., it is to be understood that the numerals represent approximate die temperatures only with the particular settings being experimentally determined. A control means for generator 79 is responsive to the signal from transducer 50 corresponding to the proper movement of catheter 10 into die 74 to produce the forming of the tip on catheter 10 so as to terminate heating of die 74. The mandrel 16 is set to finish the lead edge of catheter 10 with a severing or clipping motion resulting from its final movement into the die 74 ending with contact between the mandrel 16 and the tapered die surface 82.

Alternatively, the measuring device for determination of sufficient flow of said catheter to produce the desired tip may be a timer rather than the linear transducer 50. In such an alternative embodiment, the time the catheter 10 must be engaged with die 74 for proper tip production is determined experimentally, and a timer set to the predetermined time interval is substituted for linear transducer 50. The control means for generator 79 is responsive to a signal from the timer that the time interval for engagement of catheter 10 with die 74 has elapsed so as to terminate heating of die 74.

Die 74, and catheter 10 therein, is then cooled by the cooling liquid which continues to be circulated by pump means 77 through cooling coils 76. It has been found that with RF heating, the most efficient cooling of die 74 occurs when the cooling means is operated continuously, and thus the cooling liquid is circulated throughout the entire tipping operation.

As the die 74 is cooled, the temperature therein continues to be monitored by the infrared sensor 107. Signals therefrom are provided to the control means including a third adjustable temperature control 122. Temperature control 122 is set to an experimentally determined value which is selected so as to provide adequate solidification of catheter 10 to permit its withdrawal from die 74. Upon reaching a temperature within die 74 that corresponds with the setting of temperature control 122, the control means deenergizes solenoid 116 so as to actuate valve 108 to direct compressed air from air supply 98 into the upper portion of container 115. At the same time, valve 108 vents container 110 to the atmosphere, and the air provided to container 115 forces the oil 112 therein into cylinder 114, moving piston 68 and thus air table 20. As air table 20 is moved away from die 74 by piston 68 to its original position, catheter 10 is withdrawn from die 74.

Following removal of catheter 10 from die 74, the catheter 10 may be removed from the mandrel 16. Another catheter may then be mounted upon mandrel 16, and the tipping process may be begun again.

It will be recognized that the disclosed method contains several parameters that are critical to the production of the desired tip on the catheter. One of the most important is the tension in spring 40 that provides the biasing force to catheter 10. It will be understood that the tension in spring 40 must be sufficient to bias the catheter into die 74 to provide for proper tipping, but cannot be so great as to force the catheter into the tapered portion 82 of die 74 prior to melting and flowing of the catheter tip. Such a situation would significantly decrease the reliability of the tipping process.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method of tipping by molding one end of an I.V. catheter, without any flash comprising the steps of;
   mounting a catheter to be tipped coaxially over a cantilever support mandrel carried on a carriage whereby said catheter is even with or extends slightly beyond the end of said mandrel,
   heating a die having an interior molding surface at least one portion of which is tapered according to the tip desired on said catheter and is open at both ends for allowing flow of catheter material therethrough,
   moving said carriage along a guide means toward said die such that said catheter carrying mandrel enters said die and carries said catheter toward engagement with said tapered molding surface,
   continuing moving said mandrel into said die and forcing said catheter into the space being established between and by the mandrel and the tapered molding surface of said die,
   allowing said catheter to heat and flow in and through said space between the tapered molding surface of the die and the mandrel and flow there through between the end of the mandrel and along the tapered die surface toward said open end,
   advancing said flowing heated catheter and carrying mandrel until said mandrel engages said interior tapered molding surface,
   severing the flowing tip of said catheter where said mandrel engages said interior tapered molding surface to ultimately define said space and the catheter tip shape as a continuous fine edge and to allow the flow of catheter material beyond said mandrel and to said open end of said die,
   cooling said die and said catheter while holding said catheter in said space defined by said mandrel and said tapered die surface,
   reversing said carriage along said guide such that said catheter is withdrawn from said die, and
   removing said catheter from said mandrel.

2. The method of claim 1 wherein the engaging of said mandrel with said tapered molding surface of said die defines the leading edge of the mandrel to form the flashless tip of said catheter.

3. The method of claim 1 further comprising measuring the temperature of said catheter material during heating and melting to determine the forcing of said catheter into said die.

4. The method of claim 1 comprising measuring the temperature of said die to determine the cooling of said catheter in the space defined between the mandrel and the tapered die molding surface.

5. Apparatus for tipping one end of an I.V. catheter to provide a fine edge for ease of penetration, comprising:
- a die defining an interior molding surface therein having at least one portion of which is tapered according to the outer surface of the tip desired on said catheter and being open at both ends for allowing flow of catheter material therethrough,
- means for controllably heating said die to a temperature sufficient to cause said catheter material to melt and flow therein and therethrough,
- means for cooling said die,
- a mandrel for supporting and carrying said catheter thereon in position even with or extending slightly cantilever therefrom,
- transport means for supporting and carrying said mandrel and catheter, movable along a predetermined path for inserting said catheter and mandrel toward said die and for removing same from said die following production of the desired tip,
- means for biasing said mandrel and said catheter inwardly with respect to said die, with sufficient force first causing said catheter to move inwardly with respect to said die as said catheter is heated to its melting point and begins to flow and then causing said mandrel to touch said die to clip the flow of catheter material which extends slightly cantilever to form a continuous finished edge at the tip of said catheter leaving the catheter end open and allowing the outward flow of the clipped catheter material to pass through said open end of said die.

6. Apparatus as defined in claim 5 wherein said transport means comprises a carriage for supporting and carrying said mandrel, and a frictionless surface for carrying said carriage, said frictionless surface being movable within guide means.

7. Apparatus as defined in claim 5 further comprising a measurement device for determining sufficient flow of said catheter within said die to produce the desired tip thereon, and control means responsive to said measurement device for controlling said heating means and reversible drive means so as to terminate heating of said die and remove said catheter therefrom following production of the desired tip.

* * * * *